(12) United States Patent
Sundholm et al.

(10) Patent No.: US 12,042,373 B1
(45) Date of Patent: Jul. 23, 2024

(54) GRAFT TRUSSING AND SUSPENSION CONSTRUCT

(71) Applicant: RIVERPOINT MEDICAL, LLC, Portland, OR (US)

(72) Inventors: Aaron Sundholm, Portland, OR (US); Edwin Anderson, Ridgefield, WA (US)

(73) Assignee: Riverpoint Medical, LLC, Portland, OR (US)

( * ) Notice: Subject to any disclaimer, the term of this patent is extended or adjusted under 35 U.S.C. 154(b) by 832 days.

(21) Appl. No.: 16/953,682

(22) Filed: Nov. 20, 2020

(51) Int. Cl.
*A61F 2/08* (2006.01)
*A61L 27/12* (2006.01)

(52) U.S. Cl.
CPC ............ *A61F 2/0811* (2013.01); *A61L 27/12* (2013.01); *A61F 2002/0894* (2013.01); *A61F 2220/0075* (2013.01); *A61F 2230/0019* (2013.01); *A61F 2240/001* (2013.01); *A61F 2250/0067* (2013.01)

(58) Field of Classification Search
CPC .. A61F 2220/0075; A61F 2/0811; A61F 2/07; A61F 2002/0894; A61F 2230/0019; A61F 2240/001; A61F 2250/0067; A61F 2/0063; A61F 2002/0068; A61F 2002/0072; A61F 2002/0874; A61F 2002/0852; A61F 2240/00; A61F 2240/0001; A61L 27/12; A61B 17/0401; A61B 2017/0404; A61B 2017/0409; A61B 2017/0495; A61B 2017/00004
See application file for complete search history.

(56) References Cited

U.S. PATENT DOCUMENTS

| | | | |
|---|---|---|---|
| 9,168,124 B2 | 10/2015 | Guerra | |
| 9,526,490 B2 | 12/2016 | Mayer et al. | |
| 10,448,943 B2 | 10/2019 | Guerra | |
| 10,786,237 B2 | 9/2020 | Guerra | |
| 2013/0197580 A1* | 8/2013 | Perriello | A61F 2/0811 606/232 |
| 2014/0194907 A1* | 7/2014 | Bonutti | A61B 17/0401 606/151 |
| 2014/0257385 A1 | 9/2014 | Lunn et al. | |
| 2016/0008123 A1* | 1/2016 | Woodruff | A61F 2/08 112/475.08 |
| 2019/0150922 A1 | 5/2019 | Amir | |
| 2019/0314143 A1* | 10/2019 | Jackson | A61F 2/0811 |
| 2020/0054316 A1 | 2/2020 | Guerra et al. | |

* cited by examiner

*Primary Examiner* — Kelly J Bekker
*Assistant Examiner* — Andrew P. Restaino
(74) *Attorney, Agent, or Firm* — BrainSpark Associates, LLC

(57) ABSTRACT

A quadricep graft suspension construct, having a button loop, including a generally rectangular button, defining four apertures, including an innermost pair of apertures; and a suture loop looping through the innermost pair of apertures. The construct also has a graft holding assembly, including a reinforcement of first fibers braided with two second fibers, and wherein the first fibers have a first and second lengthwise end and the second fibers continue separately, extending from the first lengthwise end to form a pair of first tails and from the second lengthwise end to form a pair of second tails and wherein the first tails are jointly swaged to a needle. And wherein the graft holding assembly is affixed to the suture loop at a position opposed to the button at least in part by the second tails being joined together about the suture loop and further including packaging holding the needle.

18 Claims, 8 Drawing Sheets

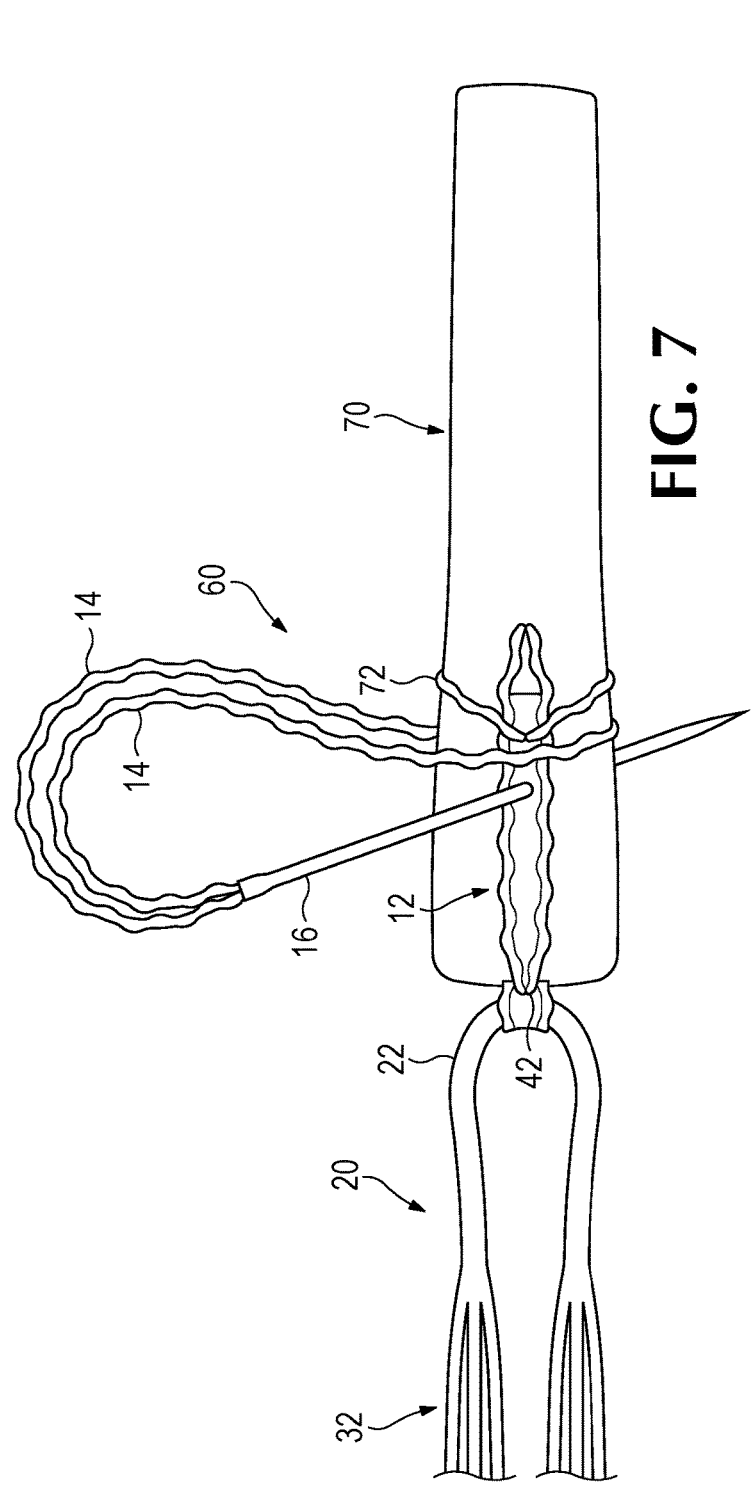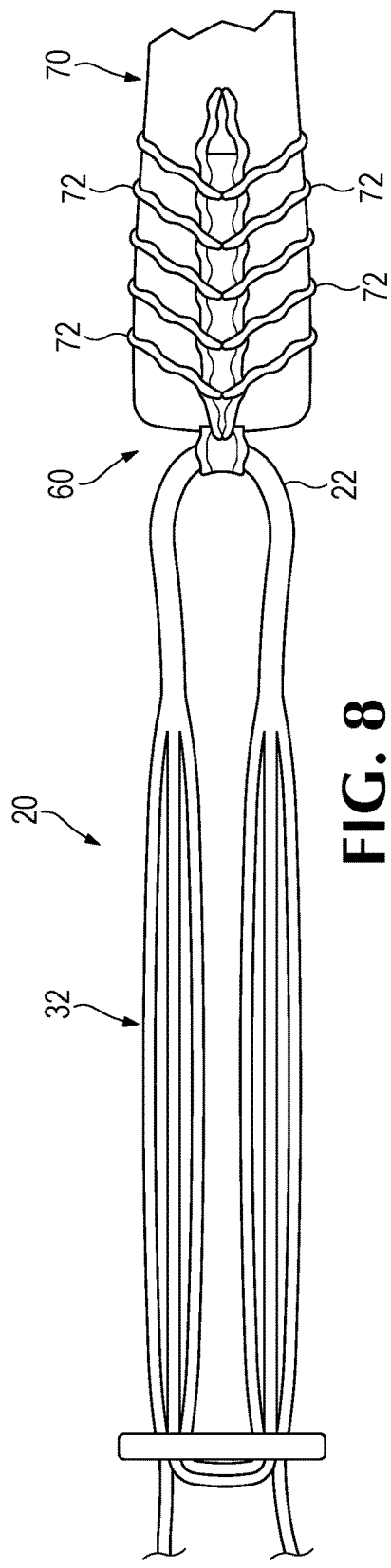

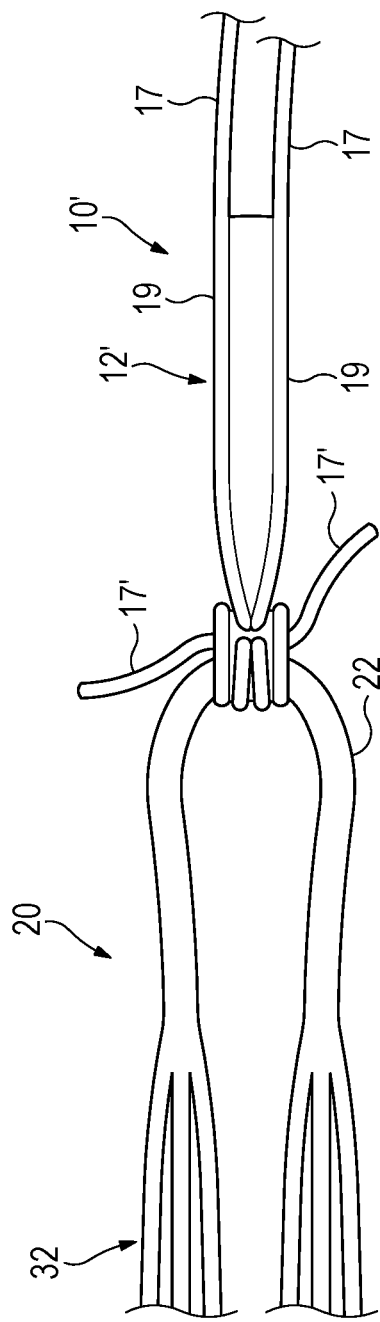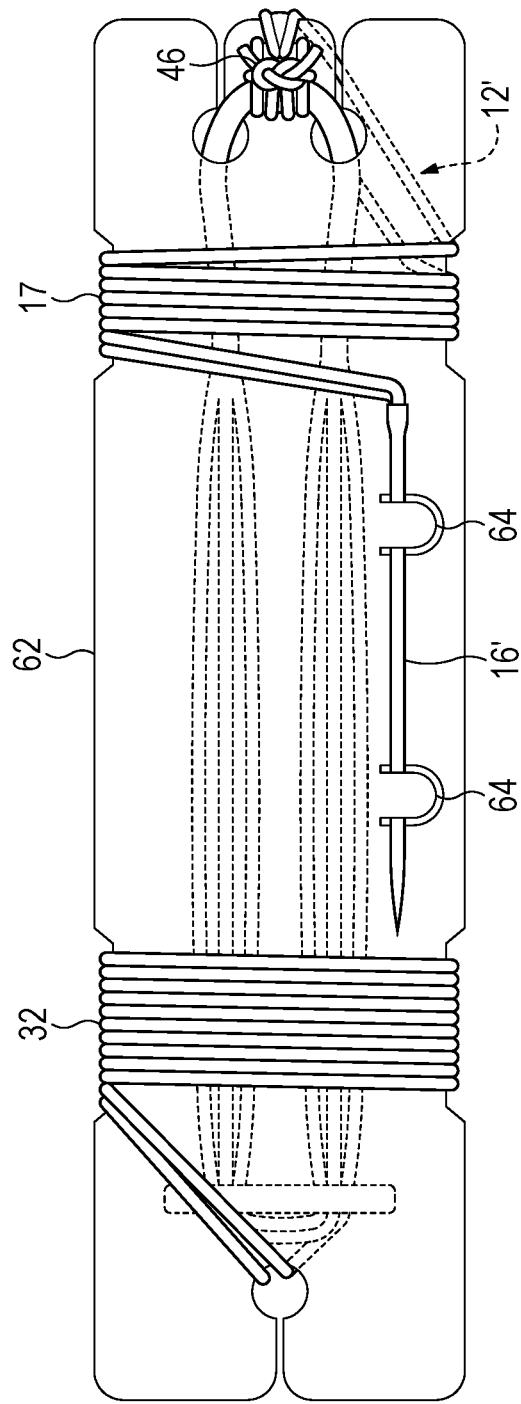

GRAFT TRUSSING AND SUSPENSION CONSTRUCT

BACKGROUND OF THE INVENTION

To perform an anterior cruciform ligament (ACL) reconstruction surgery in the knee, it is necessary supply a graft, and attach the graft to constructs for suspending the graft in a tunnel created in the femur and the tibia. The place where the graft attaches to each suspension construct will be subjected to substantial tensile force, possibly causing the suture of the suspension construct to rip through the tissue of the graft, causing a catastrophic failure of the ACL reconstruction.

Within the last few years, a graft harvested from the quadricep tendon (quad), directly above the knee has become increasingly popular, due to good graft performance, and less morbidity at the harvest site. This type of graft requires particular care, to be certain that the suture that suspends the graft at a beneficial position in the tunnel will not pull through the graft tissue. Unlike a hamstring tendon graft, a quad graft is not folded over a loop, to be doubled up (as the hamstring tendon is thinner). And unlike a patella harvested tendon, there is not bone on either side, to provide a particularly strong piece of tissue to which the suture is engaged.

Various entities have originated constructs and methods for attaching a suspension construct to a quad graft. A reinforcement element is sometimes used, to better ensure that the suture does not pull through the graft. One of the constructs requires a few extra needle pass steps to strongly affix one portion of the construct to another, during graft/construct preparation. Eliminating these steps would save medical personnel some valuable medical time during surgery preparation.

SUMMARY OF INVENTION

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

In a first separate aspect the present invention may take the form of a method of attaching a graft to a construct that utilizes a construct having a reinforcement comprising a flat braid of fibers, which has a first end and an opposed second end and wherein two of the fibers extend out of both the first end to form a pair of first tails and the second end of the reinforcement to form a pair of second tails, and wherein a needle is swaged onto the ends of the first tails, joining them together. The construct further has a button loop assembly, including a suture loop, the suture loop further being engaged to a generally rectangular button defining four apertures, by looping through two of the apertures and wherein the flat braid of fibers is attached to the suture loop at least in part by the second tails being joined together about the suture loop at a location generally opposed to the button. In the method, the reinforcement of woven fibers is placed on the graft. Then, the needle and first tails are used to whipstitch the reinforcement to the graft by starting at a first location of the reinforcement.

In a second separate aspect, the present invention may take the form of a quadricep graft suspension construct, having a button loop, including a generally rectangular button, defining four apertures, including an innermost pair of apertures; and a suture loop looping through the innermost pair of apertures. The construct also has a graft holding assembly, including a reinforcement of first fibers braided with two second fibers, and wherein the first fibers have a first and second lengthwise end and the second fibers continue separately, extending from the first lengthwise end to form a pair of first tails and from the second lengthwise end to form a pair of second tails and wherein the first tails are jointly swaged to a needle. And wherein the graft holding assembly is affixed to the suture loop at a position opposed to the button at least in part by the second tails being joined together about the suture loop and further including packaging holding the needle.

In a third separate aspect the present invention may take the form of a method of making a fiber reinforcement and needle construct that begins by braiding a group of fibers into a braid construct, the fibers including a group of first fibers and two second fibers. Then a sacrificial portion of the first fibers are removed to leave a flat braided portion with two first tails extending therefrom. Finally, a needle is swaged onto the ends of the two fibers.

BRIEF DESCRIPTION OF DRAWINGS

Various embodiments of the invention are disclosed in the following detailed description and accompanying drawings.

FIG. 7 is a plan or top view of the graft suspension construct, with the reinforcement laid upon a graft.

FIG. 8 is a plan view of a completed graft suspension construct, whipstitched to a quadricep graft.

FIG. 17 shows a penultimate step of combining the alternative needle and reinforcement component to an adjustable button loop component of a graft suspension device.

FIG. 18 shows a completed graft suspension device affixed to a packaging element.

DETAILED DESCRIPTION AND EMBODIMENTS

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

To assist the description of the scope and its components the coordinate term "under" and "over" are used to describe the disclosed embodiments. The terms are used only as relative terms, for ease of description. Accordingly, in a sequence of operations, if the first step states that a first item is placed under a second item, and the next step states that the first item, or a portion thereof, is brought over the second item, the terms "under" and "over" could be reversed, with the first step stating that first item is placed over the second item, and the second step stating the first item or a portion thereof is brought under the second item. Stated differently, "under" simply means "on a first side of" and "over" means "on a second side of, opposed to said first side." Because the terms "under" and "over" are more familiar to most readers and are less wordy and easier to understand, applicant is choosing those terms, over the more verbose terms.

Figure 1:
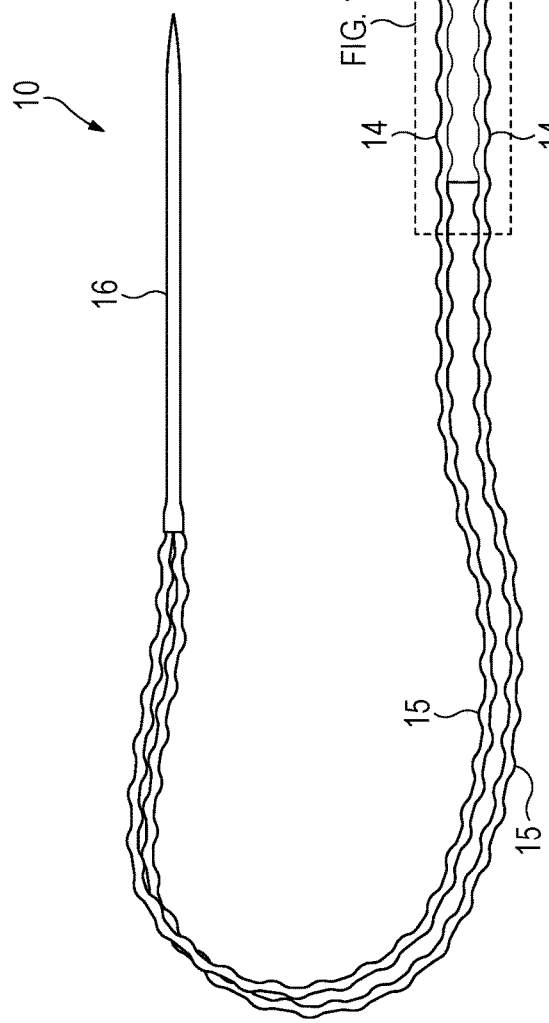
FIG. 1 is a plan view of a needle and reinforcement component of a graft suspension construct.
Figure 2:
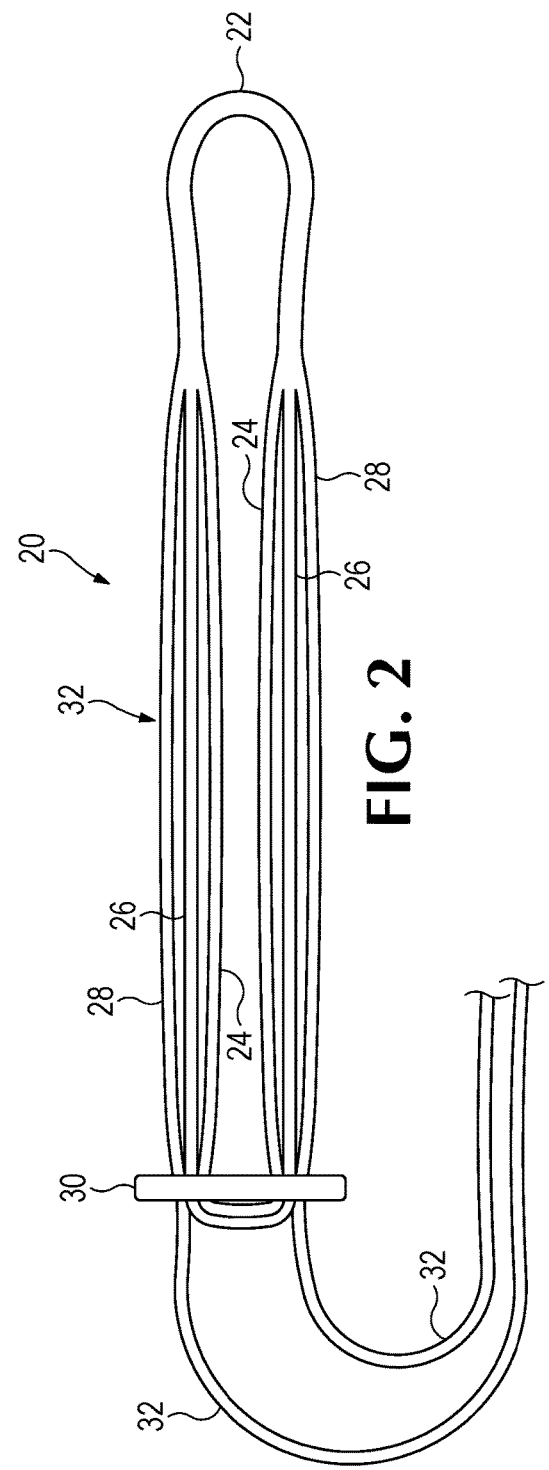
FIG. 2 is a plan view of an adjustable button loop component of a graft suspension device.

Referring to FIG. 1, a needle and reinforcement component 10 includes a reinforcement 12 that consists of a flat braid of fibers, two warp strands 14 that extend out of reinforcement 12, to form a pair of tails 15 and a needle 16 swaged onto the ends of the two tails 15. FIG. 2 shows the button loop component 20 to which component 10 will be attached. This includes a trap section 22, in which the inner length of suture 24 accepts portions of middle suture length 26 and outer suture length 28 in its lumen. Outer suture lengths 28 extend out of holes in button 30 and may be pulled on to shorten the length of triple loop 32. Skilled persons will recognize that this type of adjustable loop is used to suspend a graft into a tunnel created in the femur and tibia.

Figure 3:
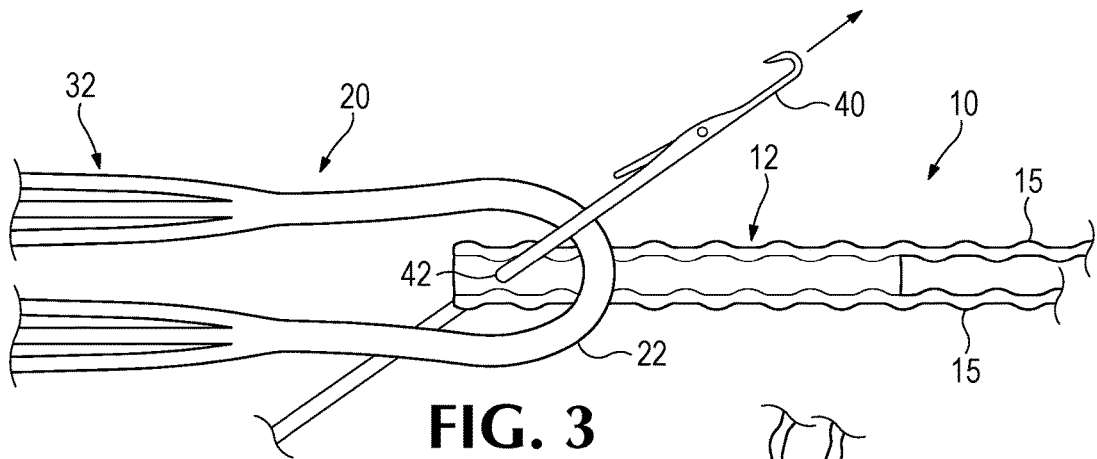
FIG. 3 is an illustration of a step in a method of attaching the needle and reinforcement component to the adjustable button loop component of the graft suspension device.
Figure 4:
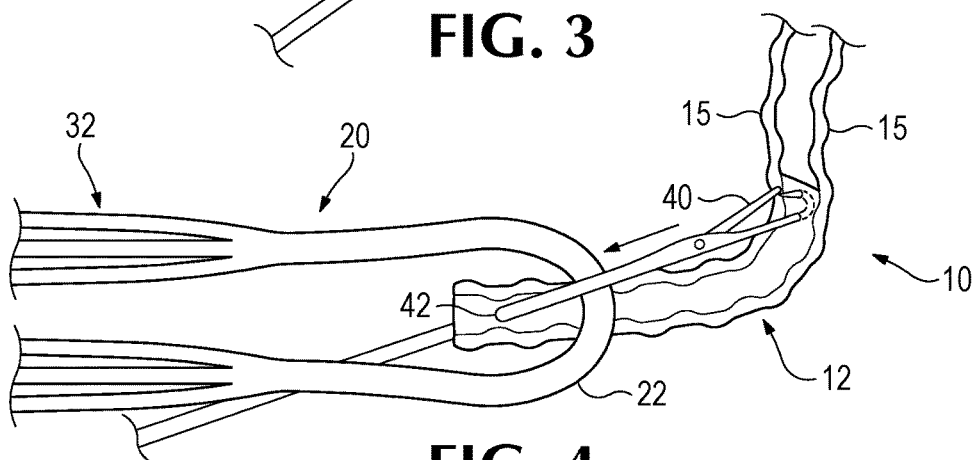
FIG. 4 is an illustration of a further step in a method of attaching the needle and reinforcement component to the adjustable button loop component of the graft suspension device.
Figure 5:
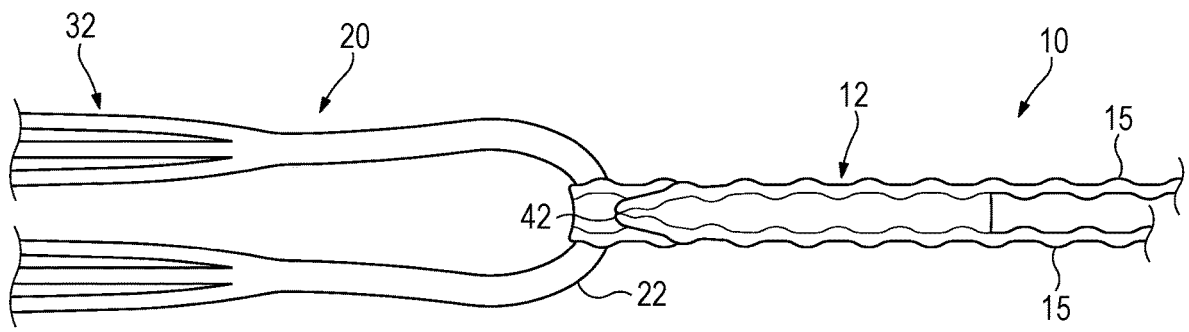
FIG. 5 is an illustration of the needle and reinforcement construct attached to the adjustable button loop component.
Figure 6:
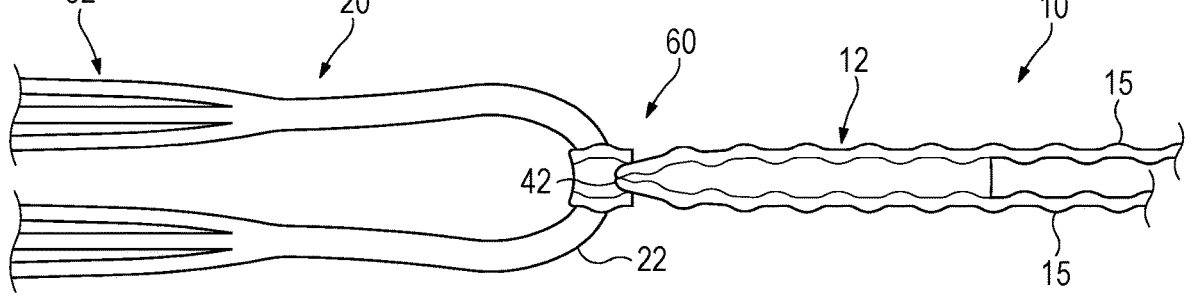
FIG. 6 is an illustration of the configuration of FIG. 5, but with some of the needle and reinforcement component cut off.

Referring, now, to FIGS. 3-6, component 10 is attached to trap section 22 of component 20, by first placing reinforcement 12 underneath trap 22 and piercing reinforcement 12 with a lacing tool 40, as shown in FIG. 3, thereby creating a broach 42 in reinforcement 12, at a position inside the triple loop 32. Next the reinforcement 12 is grabbed by lacing tool 40, as shown in FIG. 4, at a position outside of triple loop 32 and pulled over trap 22 and through broach 42. The pulling continues until the remainder of reinforcement 12, tails 15 and needle 16 are pulled through the broach 42, resulting in the configuration shown in FIG. 5. Finally, the remainder of reinforcement 12 is cut with a hot knife, with the resultant construct 60 shown in FIG. 6 and FIG. 7 (shown with graft).

As noted, FIG. 7 shows construct 60 positioned relative to a graft 70, so that reinforcement 12 is directly on top of graft 70 and with needle 16 being used to whipstitch reinforcement 12 onto graft 70, with a stitch 72, already completed. FIG. 8 shows construct 60 attached to graft 70, by means of whipstitching 72. The advantages of this configuration will now be apparent to skilled persons, as a strong construct 60 is affirmatively connected to tendon 70, with reinforcement 12 adding strength to the connection, thereby preventing tails 15 from pulling through graft 70.

Figure 9:
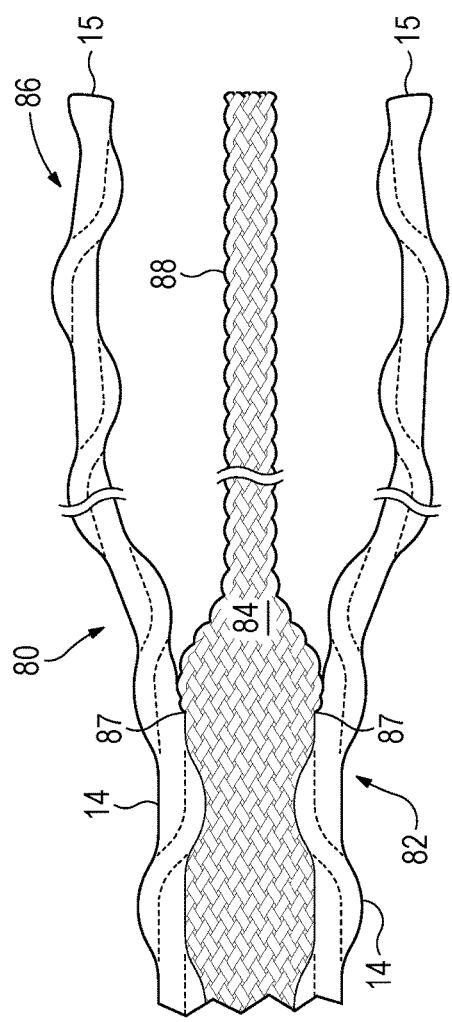
FIG. 9 is an illustration of a braid that is created and used in the construction of the needle and reinforcement component.
Figure 10:
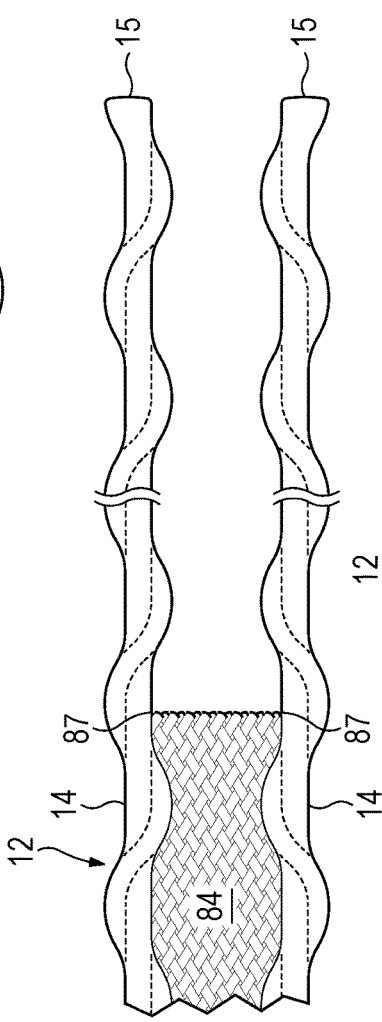
FIG. 10 is an illustration of the braid of FIG. 9, at a further stage of construction.
Figure 11:
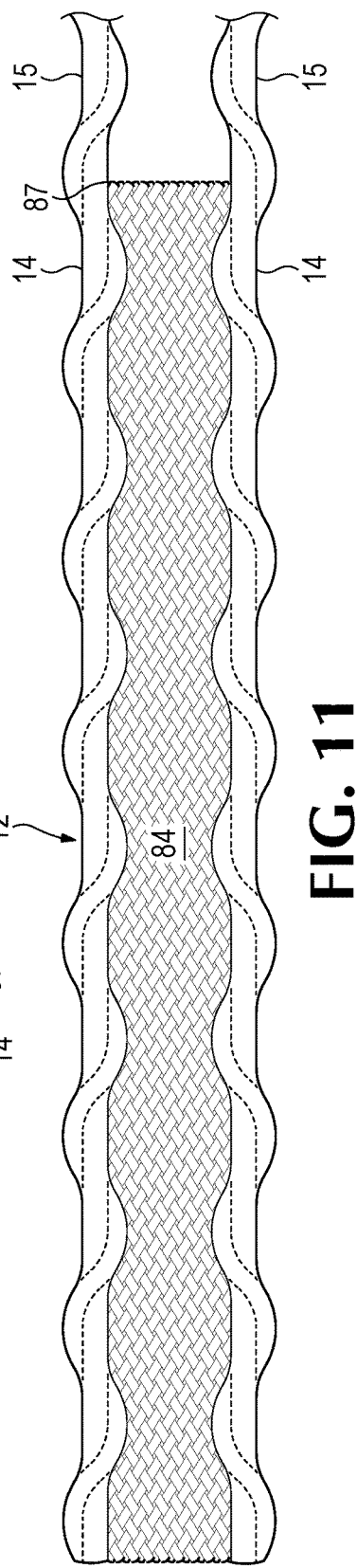
FIG. 11 is a plan view of a different portion of the stage of FIG. 10.
Figure 12:
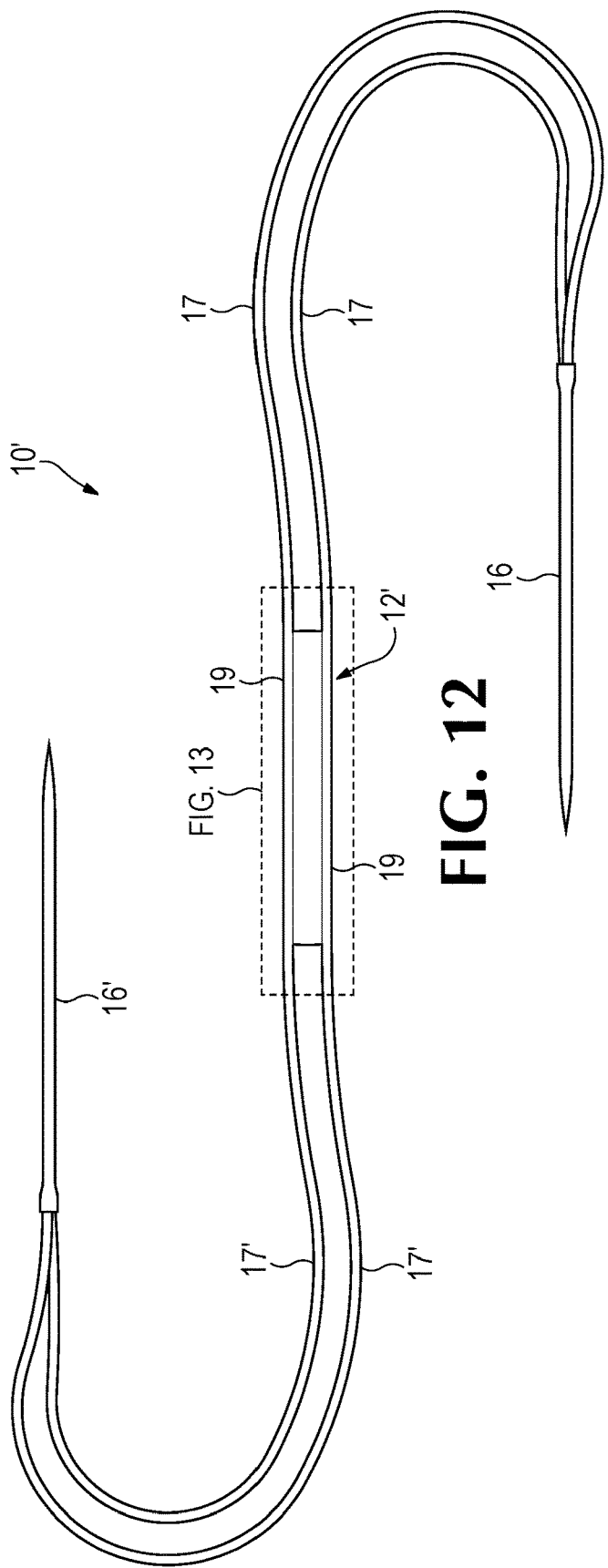
FIG. 12 is a plan view of an alternative embodiment of a needle and reinforcement component of a graft suspension construct.
Figure 13:
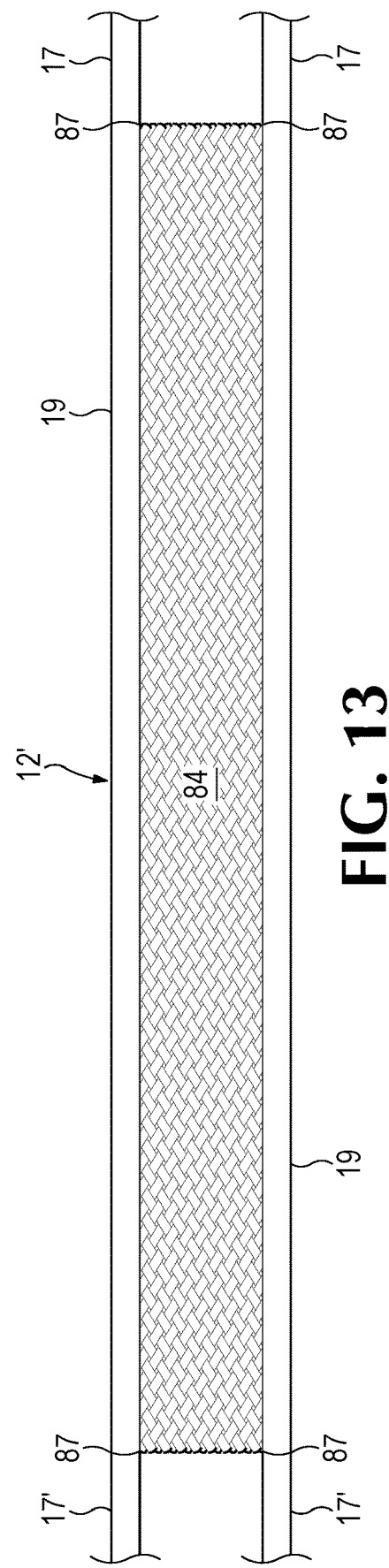
FIG. 13 is a detail view of the reinforcement portion of the component of FIG. 12.

FIGS. 9-11 show stages in the production of component 10, with FIG. 9 showing the configuration 80 after braiding by a round-to-flat braiding machine, such as those available from Herzog Maschinenfabrik GmbH & Co. of Oldenburg, Germany. Portion 82 is braided while the machine is in its flat braiding configuration, with seventeen 100 denier fibers 84 visible in the center, and two larger warp strands 14 shown at the sides, integrally braided with fibers 84. In alternative embodiments another size of fibers 84 are used. Portion 86 is braided after the braiding machine has been switched to round mode at transition point 87, so that fibers 84 are configured in a round braid 88, with warp strands 14 excluded. Then the round braid 88 is cut off at the transition point 87, as shown in FIGS. 10 and 11, thereby forming a separate reinforcement 12, with two tails 15 extending out from it. A needle 16 is swaged to the ends of the two tails 15 to result in the component 10 shown in FIG. 1.

In a preferred embodiment warp strands 14 have an irregular, somewhat helical appearance, as they are formed by co-braiding together fifteen carriers of 100 denier fiber with 1 carrier of 650 denier fiber, depending on the specific embodiment, resulting in the irregular, unbalanced and somewhat bumpy or helical appearance shown. In alternative embodiments, other sizes of fibers are used.

Figure 14:
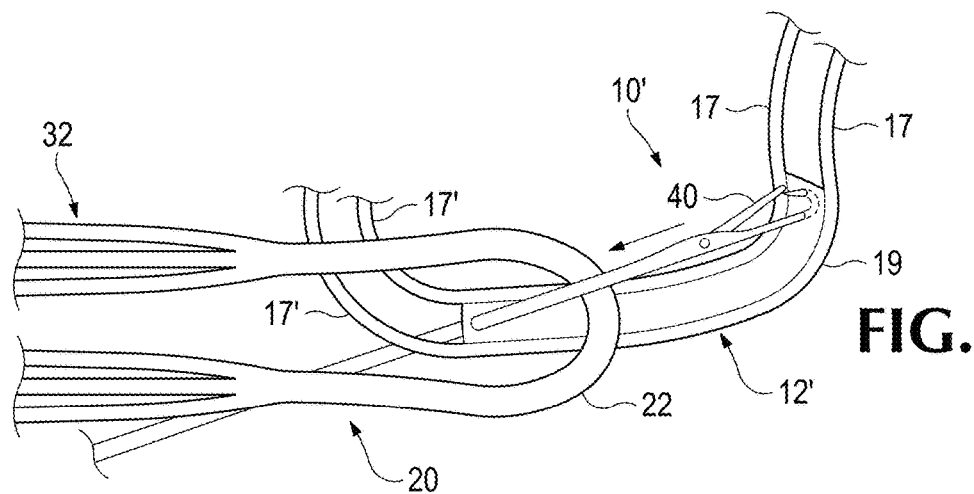
FIG. 14 shows an initial step of combining the alternative needle and reinforcement component to an adjustable button loop component of a graft suspension device.
Figure 15:
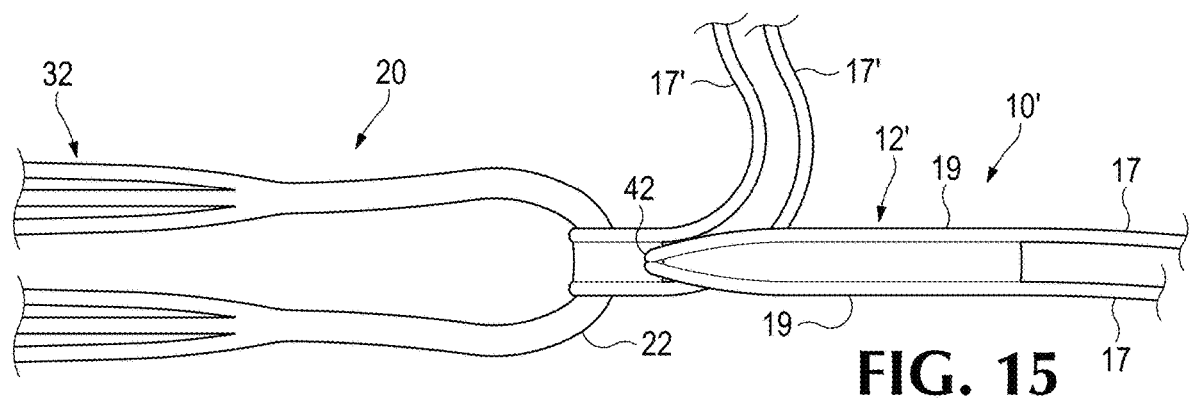
FIG. 15 shows a subsequent step of combining the alternative needle and reinforcement component to an adjustable button loop component of a graft suspension device.
Figure 16:
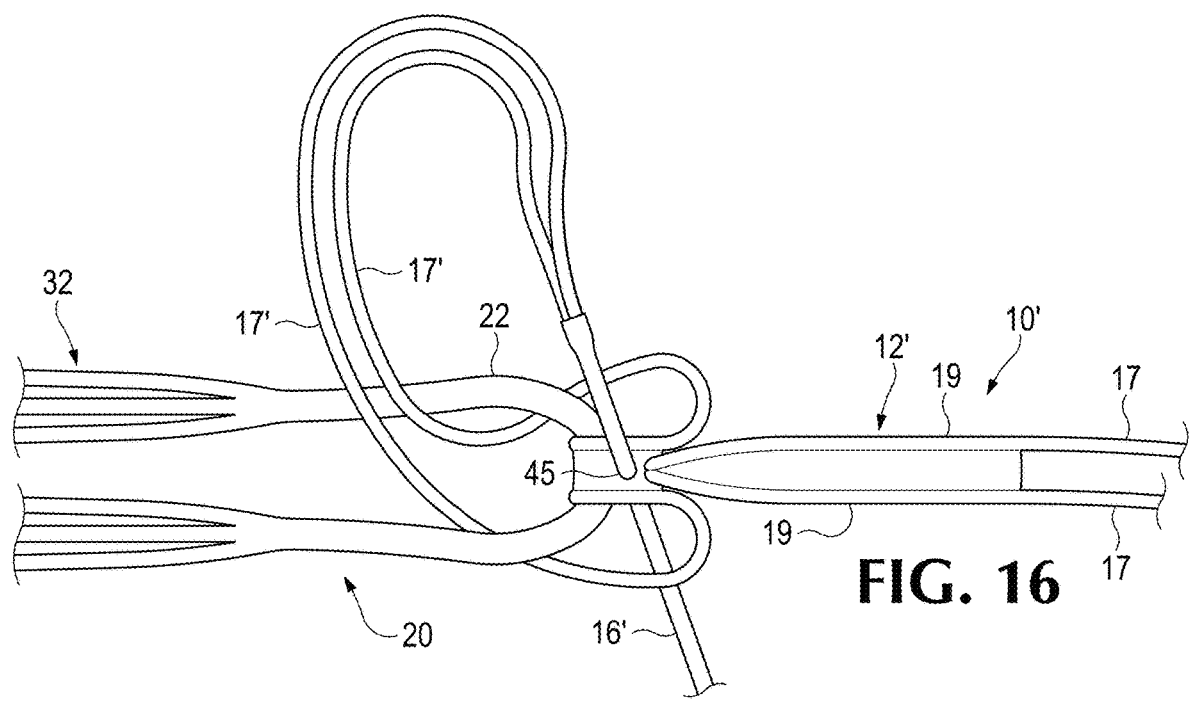
FIG. 16 shows an additional subsequent step of combining the alternative needle and reinforcement component to an adjustable button loop component of a graft suspension device.
Figure 19:
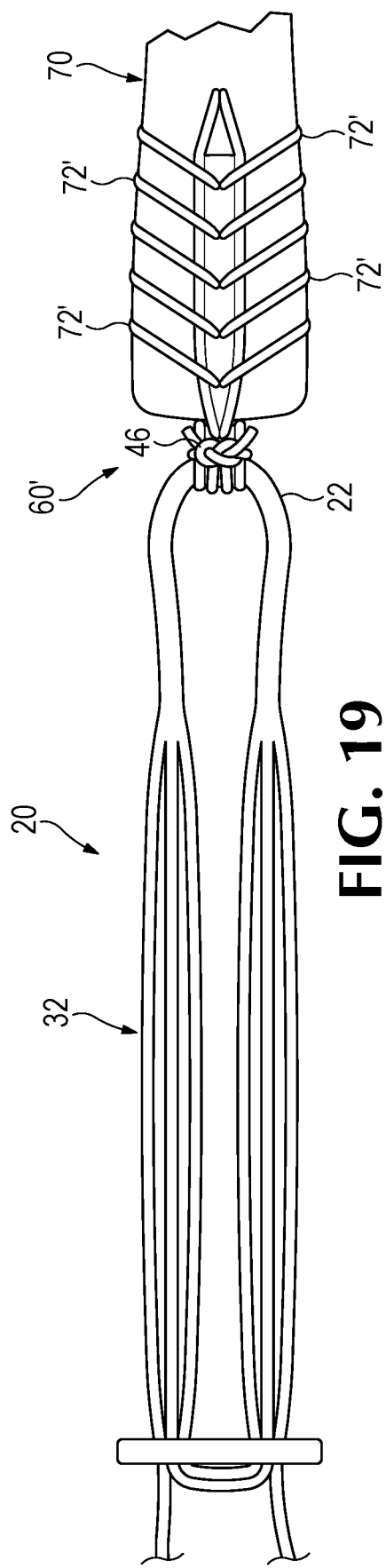
FIG. 19 shows a completed graft suspension device whipstitched onto a graft.

Referring to FIGS. 12-18, in an additional embodiment, a separate reinforcement and needle component 10' is made in a manner similar to component 10, except for that the warp strands 19 are smooth, in contrast to the bumpy warp strands 14. In an alternative embodiment bumpy warp strands 14 are used in embodiment 10' instead of smooth warp strands 19. Also, braiding begins with the braiding machine set to "round," thereby producing second tails 17' (after cutting off the round center braid at a transition point 87 [FIG. 13]), then flat, producing reinforcement 12, and then round again, producing tails 17 (similar to tails 15, but made of smooth warp strand 19). As shown, both pairs of tails 17 and 17' are swaged to a needle 16 and 16', respectively. Referring to FIGS. 14 and 15, the initial steps of attaching component 10' to component 20 is the same as for connecting component 10 to component 20, as shown in FIGS. 3 and 4. FIG. 16-18 show an additional step of buttressing the connection between components 10' and 20 by looping tails 14' about trap 22, engaging them to reinforcement 12', by piercing reinforcement 12' with swaged needle 16' and pulling both tails 14' through reinforcement 12, until looped tautly about trap 22. Referring to FIG. 18 the ends of second tails 14' are then tied together in a knot 46, to produce a finished construct 60', which as shown may be engaged to packaging 62, in which needle 16' is safely retained by tabs 64. FIG. 19 shows whipstitching 72, joining construct 60' onto quadricep graft 70.

In embodiments, the warp strands 14 and 84 are made of a combination of absorbable material, such as polycaprolactone, polyester amides, modified polyethylene terephthalate, polylactic acid and its copolymers, terpolymers based on polylactic acid, polyglycolic acid, polyalkyline carbonates (e.g., polyethylene carbonate, poly(glycolideco-trimethylene carbonate, etc.), polyhydroxyalkanoates, poly-3-hydroxybutyrate, poly-20 3-hydroxyvalerate, poly-3-hydroxybutyrate-co-4-hydroybutyrate, poly-3-hydroxybutyrate-co-3-hydroxyvalerate copolymers, poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate based aliphatic polymers e.g., polybutylene succinate, as noted below, polybutylene succinate adipate, polyethylene succinate, etc. Anyone of the above materials could be mixed with hydroxyapatite, a bone growth stimulant, to encourage the tunnel drilled in the femur and tibia to have ingrowth into the fiber, thereby promoting healing. Notably, hydroxyapatite has good biocompatibility, bioactivity and osteoconductivity. In further embodiments these qualities are used, with hydroxyapatite utilized as a scaffold for drug and/or bone growth agent delivery. That is to say that a drug or further bone growth agent or agents is mixed with the hydroxyapatite in the fiber. In further embodiments, a high strength material, such as ultra-high molecular weight polyethylene is included, particularly where high strength is needed, for example in fibers 17 or 19.

The system and method described above provides unsurpassed ease of use and certainty of proper healing.

The disclosed embodiments are illustrative, not restrictive. While specific configurations of the graft suspension construct have been described, it is understood that the present invention can be applied to a wide variety of tissue holding constructs. There are many alternative ways of implementing the invention.

What is claimed is:

1. A method of attaching a graft to a construct, comprising:
    a) providing a construct having:
        i. a reinforcement section comprising a flat braid of fibers including a fiber diameter, a first strand with a first strand diameter, and a second strand with a second strand diameter, said reinforcement section having a first end and an opposed second end, said flat braid of fibers extending between said first strand and said second strand, said first strand diameter and said second strand diameter being different than said fiber diameter;
        ii. two of said fibers said first strand and said second strand extending out of both said first end to form a pair of first tails and said first strand and said second strand extending out of said second end to form a pair of second tails, and wherein a needle is connected to the ends of said first tails; and
        iii. a button loop assembly, including a suture loop, said suture loop further being engaged to a button defining two or more apertures, by looping through two of said two or more apertures;
        iv. wherein at least a portion of said flat braid of fibers is attached to said suture loop at least in part by said second tails being joined together about said suture loop at a location opposed to said button;
    b) placing at least a portion of said reinforcement section of woven fibers on said graft;
    c) using said needle and said first tails to whipstitch said at least a portion of said reinforcement section to said graft by starting at a first location of said reinforcement section.

2. The method of claim 1, wherein said flat braid of fibers is further attached to said suture loop by said flat braid of fibers being drawn though itself at a broach point, to form a loop about a location of said suture loop and cinched tight.

3. The method of claim 2, wherein said suture loop is length adjustable.

4. The method of claim 1, wherein the at least a portion of said flat braid of fibers comprises hydroxyapatite.

5. The method of claim 4, wherein the at least a portion of said first set of flat braid of fibers are made of comprises an absorbable fiber material, impregnated with the hydroxyapatite.

6. The method of claim 5, wherein said hydroxyapatite comprises a bone growth agent.

7. The method of claim 5, wherein said hydroxyapatite comprises a drug.

8. The method of claim 1, wherein said second tails are looped around said suture loop, prior to being joined together.

9. The method of claim 1, wherein said second tails are joined together by being tied together, in a knot.

10. The method of claim 1, wherein said first strand and second strand are co-braided with the flat braid of fibers.

11. The method of claim 1, wherein said first strand and second strand comprise an irregular shape.

12. The method of claim 11, wherein the irregular shape comprises a helical, bumpy or twisted shape.

13. The method of claim 1, wherein the reinforcement section comprises a flat, planar shape.

14. The method of claim 1, wherein the first strand and the second strand comprise a round suture.

15. The method of claim 1, wherein the first strand and the second strand comprise ultra-high molecular weight polyethylene.

16. The method of claim 1, wherein the first strand and the second strand comprise an absorbable material.

17. The method of claim 16, wherein the absorbable material comprises hydroxyapatite.

18. The method of claim 17, wherein the hydroxyapatite comprises a bone growth agent.

* * * * *